(12) United States Patent
Laux et al.

(10) Patent No.: US 8,394,982 B2
(45) Date of Patent: Mar. 12, 2013

(54) METHOD AND PLANT FOR PURIFYING UNSATURATED COMPOUNDS

(75) Inventors: Benedikt Laux, Monzernheim (DE); Christian Maul, Neustadt a.d.W. (DE); Volker Schleep, Einhausen (DE); Ingo Sander, Shanghai (CN)

(73) Assignee: Evonik Röhm GmbH, Darmstadt (DE)

( * ) Notice: Subject to any disclaimer, the term of this patent is extended or adjusted under 35 U.S.C. 154(b) by 336 days.

(21) Appl. No.: 12/677,540

(22) PCT Filed: Aug. 29, 2008

(86) PCT No.: PCT/EP2008/061359
§ 371 (c)(1),
(2), (4) Date: Mar. 11, 2010

(87) PCT Pub. No.: WO2009/065633
PCT Pub. Date: May 28, 2009

(65) Prior Publication Data
US 2010/0217030 A1   Aug. 26, 2010

(30) Foreign Application Priority Data
Nov. 23, 2007 (DE) .................. 10 2007 056 926

(51) Int. Cl.
*C07C 67/54* (2006.01)
*C07C 69/54* (2006.01)
*B01D 1/22* (2006.01)

(52) U.S. Cl. ....................... 560/209; 560/218

(58) Field of Classification Search ............... None
See application file for complete search history.

(56) References Cited

U.S. PATENT DOCUMENTS

| 6,380,424 B1 | 4/2002 | Yoneda et al. |
| 2006/0211880 A1 | 9/2006 | Ackerman et al. |

FOREIGN PATENT DOCUMENTS

| CN | 1317021 | 10/2005 |
| EP | 1 090 904 | 4/2004 |
| WO | 00 08072 | 2/2000 |
| WO | WO 00/08072 | 2/2000 |
| WO | 2004 063140 | 7/2004 |

OTHER PUBLICATIONS

Chinese Office Action issued Aug. 3, 2012, in Chinese Patent Application No. 200880107422.1 (with English-language Translation).

*Primary Examiner* — Yevegeny Valenrod
(74) *Attorney, Agent, or Firm* — Oblon, Spivak, McClelland, Maier & Neustadt, L.L.P.

(57) ABSTRACT

A process for purifying an unsaturated compound, where purification is performed in a plant with evaporators.

26 Claims, 1 Drawing Sheet

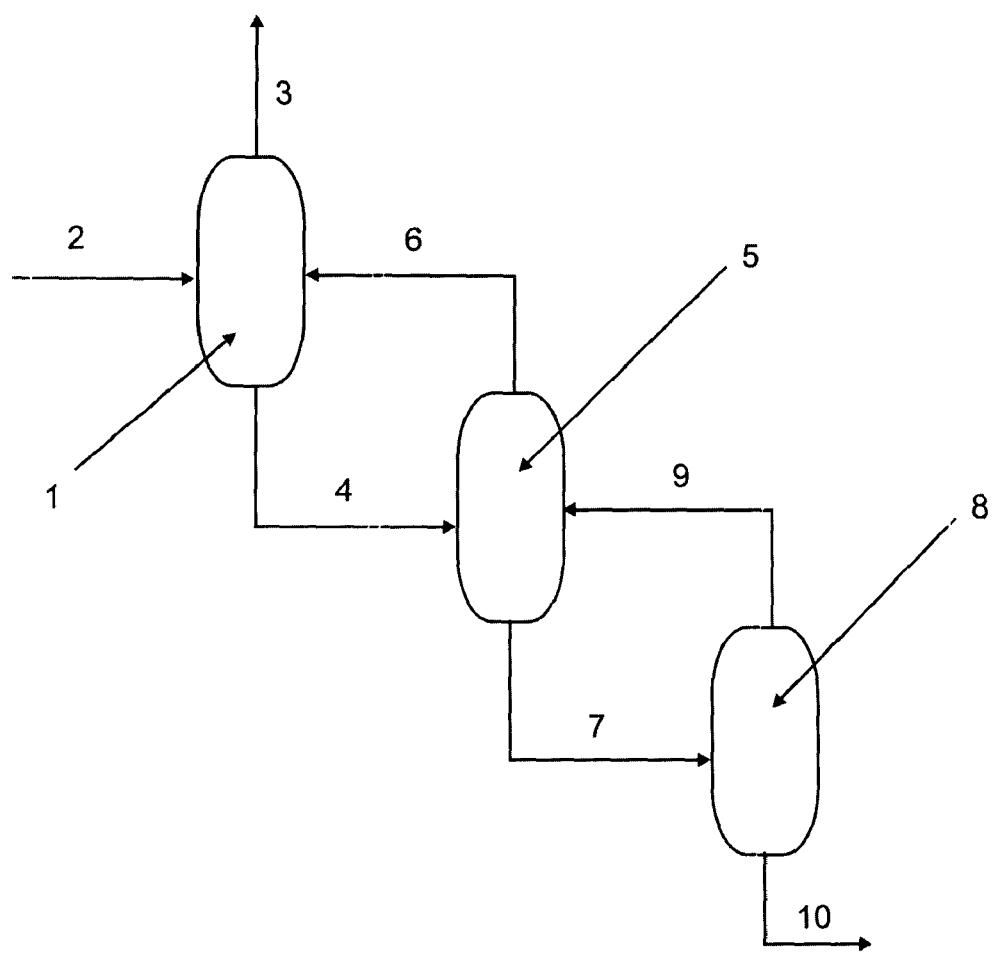

METHOD AND PLANT FOR PURIFYING UNSATURATED COMPOUNDS

This application is a 371 of PCT/EP2008/061359 filed Aug. 29, 2008.

The present invention relates to a process for purifying unsaturated compounds. The present invention further describes a plant for performing the present process.

Unsaturated compounds of high boiling point tend to form by-products in the course of purification. This gives rise to various problems in connection with the isolation of these compounds. For example, polymerization of the unsaturated products can form deposits in the purification plants. In order to ensure a high quality of the product, it is therefore necessary to clean these plants from time to time.

STATE OF THE ART

Furthermore, the formation of by-products leads to a reduction in the overall yield. In the case of purification in a still with one column which, owing to fewer internals, has a low pressure drop, these problems can be avoided. However, it is not possible to achieve optimal separation performance in this way. On the other hand, it is in many cases necessary to provide a product of maximum purity. The particularly problematic compounds include especially glycol esters, for example hydroxyalkyl (meth)acrylates. In addition to polymers, these compounds form di(meth)acrylates, which are particularly undesired. In order to solve the problems detailed above, efforts have already been made.

For example, the publication CN1502601 describes a process for purifying hydroxyalkyl (meth)acrylates, which has several stages. In this case, the individual stages are connected in series. In a first thin-film evaporator, the nonvolatile compounds are removed. The evaporated product is condensed and passed into a falling-film evaporator. In the falling-film evaporator, the compound to be purified is freed of volatile constituents. In a further thin-film evaporator, the product is drawn off via the top, and nonvolatile constituents are recycled to the first thin-film evaporator with a low product content. The product is accordingly not circulated. A hydroxypropyl methacrylate which has been purified by the process described in the publication CN1502601 exhibited a purity of approx. 98.7%.

Furthermore, document EP-A-1 090 904 describes a process for purifying hydroxyalkyl (meth)acrylates. In this process, a still is used together with a thin-film evaporator, and the bottoms of the still are introduced into the thin-film evaporator. The column of the still has no internals which lead to a pressure drop. These measures can achieve the effect that the purified product has a relatively high purity with a low diester content. As compared with a simple distillation, however, the purity increases only insignificantly from 98.1 to 98.5%. It is essential in this context that the residence time can be kept short. The recycling of a large amount of evaporated product from the thin-film evaporator into the still is not described in quantitative terms.

The processes detailed above already show an improvement over the conventional prior art. However, there is the permanent need to further improve the purity and the yield of the unsaturated compounds.

Problem

In view of the prior art, it is thus an object of the present invention to provide processes for purifying unsaturated compounds, which lead to particularly pure products in a high yield.

It is a further object of the invention, more particularly, to provide a process in which the formation of by-products in the course of purification is particularly low. More particularly, the process in the plants for purification should lead only to low formation of deposits. This should enable long-term operation of the plant, without any need for operation of the plant to be interrupted owing to cleaning measures.

Furthermore, the process should be performable in a very simple and inexpensive manner.

Furthermore, it was therefore an object of the present invention to provide a plant for performing a corresponding process. At the same time, the plant should be cleanable in a simple manner.

Solution

These objects, and also further objects which are not stated explicitly but which are immediately derivable or discernable from the connections discussed herein by way of introduction, are achieved by a process having all features of claim 1. Appropriate modifications of the process according to the invention are protected in subclaims. With regard to the plant for performing the process, claim 20 provides a solution to the problem.

The present invention accordingly provides a process for purifying unsaturated compounds, said purification being performed in a plant which comprises at least two evaporators which are connected in such a way that a portion of the unsaturated compound is circulated, the vapours condensed in the first evaporator being isolated and the vapours condensed in the second evaporator being introduced into the first evaporator, which is characterized in that the mass flow with which the condensed vapours are isolated from the mixture to be purified in the first evaporator is less than the mass flow with which the condensed vapours from the second evaporator are introduced into the first evaporator.

It is thus possible in an unforeseeable manner to provide a process of the type described above which has a particularly good profile of properties. Surprisingly, it is possible to obtain, in particular, products with a particularly high purity in a very good yield.

Moreover, the formation of by-products in the purification is particularly low. In this context, the process in the plants for purification leads only to low formation of deposits. This makes possible long-term operation of the plants, without any need for the operation of the plant to be interrupted.

Furthermore, the process according to the invention can be performed in a very simple and inexpensive manner.

The present invention further provides a plant for performing a corresponding process, the plant being cleanable in a simple manner.

The process of the present invention serves especially for purifying unsaturated compounds which have at least one carbon-carbon double bond. Of particular interest are especially compounds which, in particular, have a boiling point at 1013 mbar of approx. 150° C. to approx. 300° C. Appropriately, the process according to the invention can be used, in particular, to purify glycol esters. These include, for example, hydroxyalkyl (meth)acrylates such as 2-hydroxyethyl (meth) acrylate, hydroxypropyl (meth)acrylate and isomers, hydroxybutyl (meth)acrylate and isomers, and also mixtures of the aforementioned compounds. The preparation of these compounds is common knowledge, valuable information being available, in particular, in the prior art cited above. For instance, these compounds can be obtained, in particular, by the reaction of (meth)acrylic acid with epoxides, for example ethylene oxide or propylene oxide.

The purification can be effected in the presence of stabilizers, which can in many cases be used actually for the preparation of the unsaturated compounds. Many mixtures for separation therefore already comprise these compounds, though they may optionally be added. The preferred stabilizers include phenol compounds, for example hydroquinone, methylhydroquinone, tert-butylhydroquinone, 2,6-di-tert-butylhydroquinone, 2,5-di-tert-butylhydroquinone, 2,4-dimethyl-6-tert-butylphenol and hydroquinone monomethyl ether; p-phenylenediamines, for example N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N,N'-di-phenyl-p-phenylenediamine, and N,N'-di-2-naphthyl-p-phenylenediamine; amines, for example thiodiphenylamine and phenothiazines; copper dialkyldithiocarbamates, for example copper dibutyldithiocarbamate, copper diethyldithiocarbamate and copper dimethyldithiocarbamate; nitroso compounds, for example nitrosodiphenylamine, isoamyl nitrite, N-nitrosocyclohexylhydroxylamine, N-nitroso-N-phenyl-N-hydroxylamine and salts thereof; and N-oxyl compounds, for example 2,2,4,4-tetramethylazetidine 1-oxyl, 2,2-dimethyl-4,4-dipropylazetidine 1-oxyl, 2,2,5,5-tetramethylpyrrolidine 1-oxyl, 2,2,5,5-tetramethyl-3-oxopyrrolidine 1-oxyl, 2,2,6,6-tetramethylpiperidine 1-oxyl, 4-hydroxy-2,2,6,6-tetramethylpiperidine 1-oxyl, 6-aza-7,7-dimethylspiro[4,5]decane 6-oxyl, 2,2,6,6-tetramethyl-4-acetoxypiperidine 1-oxyl and 2,2,6,6-tetramethyl-4-benzoyloxypiperidine 1-oxyl. These compounds may be present in the mixture for purification preferably in an amount in the range from 0.0001% by weight to 1% by weight, more preferably in the range from 0.0005% by weight to 0.5% by weight.

The purification is carried out in a plant which comprises at least two evaporators. In the context of the present invention, the expression "evaporator" refers to an apparatus which is suitable for converting the unsaturated compounds to the gas phase. These include, more particularly, thin-film evaporators, for example falling-film evaporators and evaporators with a rotating wiper system, and also circulation evaporators, for example forced- or natural-circulation evaporators. It is also possible to use short-path evaporators. Such apparatus is known (cf. Ullmanns Encyclopedia of Industrial Chemistry (6th edition), Verlag Wiley-VCH, Weinheim 2003, volume 36, page 505).

In the plant for performing the process according to the invention, at least two evaporators are connected such that a portion of the unsaturated compound can be circulated, the vapours condensed in the first evaporator being isolated and the vapours condensed in the second evaporator being introduced into the first evaporator. As already explained, the evaporators are connected to one another in such a way that a portion of the unsaturated compounds can be circulated. This means that the portion of the composition which remains in the first evaporator and has not been converted to the gas phase is transferred into the second evaporator, for example into the bottom. These bottoms comprise, in particular, a high proportion of nonvolatile compounds. According to the invention, the mass flow with which the condensed vapours are isolated from the mixture to be purified in the first evaporator is less than the mass flow with which the condensed vapours from the second evaporator are introduced into the first evaporator. Of particular interest are especially processes in which the ratio of the mass flow with which the condensed vapours are isolated (3) from the mixture to be purified in the first evaporator to the mass flow with which the condensed vapours from the second evaporator are introduced (6) into the first evaporator is preferably in the range from 0.4 to 1.5, more preferably in the range from 0.5 to 0.8. It is evident from this that a high proportion of the compositions (2) introduced into the first evaporator is introduced (4) into the second evaporator via the bottom. This proportion is determined from the ratios of the two mass flows detailed above.

In a particular embodiment, the process according to the invention can be carried out in a plant which comprises at least three evaporators, in which case one circuit between the first and the second evaporator (4 & 6) and one circuit between the second and the third evaporator (7 & 9) are formed, the embodiments detailed above regarding the circuits applying correspondingly.

In this case, the ratio of the mass flow with which the condensed vapours from the second evaporator are introduced (6) into the first evaporator to the mass flow with which the condensed vapours from the third evaporator are introduced (9) into the second evaporator is preferably in the range from 0.75 to 35, more preferably in the range from 2 to 10. By virtue of this embodiment of the process according to the invention, it is surprisingly possible, in particular, to increase the yield.

The mixture to be purified can preferably be introduced into the first and/or the second evaporator. Of particular interest are especially processes in which at least a portion of the mixture to be purified is first introduced into the first evaporator and a further portion of the mixture to be purified is first introduced into the second evaporator.

Appropriately, the mass flow ratio of the portion of the mixture to be purified introduced into the first evaporator to the portion of the mixture to be purified introduced into the second evaporator may preferably be in the range from 9:1 to 0.1:1, more preferably in the range from 8:1 to 2:1.

The type of evaporator is in principle of minor importance for the performance of the process according to the invention. However, it has been found to be appropriate that a circulation evaporator is used as the first and second evaporator. The third evaporator used is preferably a thin-film evaporator.

The purification process according to the invention can be conducted within a wide pressure and temperature range. In order to minimize the formation of by-products, it is appropriate to keep the temperature at a low level. Accordingly, the process according to the invention is preferably conducted at a low pressure. On the other hand, the maintenance of a very low pressure is found to be very costly and inconvenient.

Particularly appropriately, the unsaturated compound is therefore converted to the gas phase preferably at a pressure in the range from 0.1 mbar to 20 mbar, more preferably in the range from 1 mbar to 10 mbar.

Temperatures needed in this case can be found from the vapour pressure curve of the particular unsaturated compound. In general, these temperatures at which the unsaturated compounds are converted to the gas phase are preferably within the range from 50° C. to 150° C., more preferably 60° C. to 110° C.

In a particular aspect of the present invention, the first evaporator is preferably operated at a gas loading factor of 1.5 to 2 $Pa^{0.5}$. Appropriately, the gas loading factor at which the first evaporator is operated is preferably in the range from 0.8 to 3.0 $Pa^{0.5}$. The gas loading factor (F factor) is calculated from the gas velocity based on the empty cross section of the tube for removing the gas multiplied by the square root of the gas density (cf. Klaus Sattler, Till Adrian, Thermische Trennverfahren [Thermal Separation Processes] (3rd edition), VCH-Verlag, Weinheim 2001, page 234).

The present invention further provides a preferred plant for performing the process according to the invention. An inventive plant comprises at least three evaporators which are connected to one another such that the residue of the first evaporator remaining in the liquid phase can be passed into the second evaporator, the condensed vapours of the second evaporator can be passed into the first evaporator and the residue of the second evaporator remaining in the liquid phase can be passed into the third evaporator, and the condensed vapours of the third evaporator can be passed into the second evaporator.

In a particular embodiment of the present plant, it has at least two circulation evaporators and one thin-film evaporator. Appropriately, the mixture to be purified is first passed into the circulation evaporator, in which case a thin-film evaporator is preferably used as the third evaporator.

The vapours generated in the evaporators can be passed into the further constituents of the plant by means of customary connections. In general, it is possible in particular to use tubes in order to remove the gas after the evaporation. Each evaporator preferably has a column, such that the plant comprises at least three columns. The term "column" should be understood here in a comprehensive sense, such that it also encompasses simple tubes. In a particular aspect of the present invention, it is possible in particular to use columns with a diameter of 0.05 m to 5 m, more preferably in the range from 0.3 m to 3 m. Appropriately, it is possible here especially to use columns which bring about a low pressure drop. Of particular interest are especially columns which, at an F factor in the range from 0.8 to 3.0 $Pa^{0.5}$, preferably in the range from 1.5 to 2.0 $Pa^{0.5}$, lead to a pressure drop in the range from 0.5 to 10 mbar, preferably in the range from 1 to 5 mbar. Accordingly, preference is given to using columns which have no packings or internals. However, this excludes droplet separators (demisters), which serve to retain compounds which generally do not evaporate under the conditions selected, but can be entrained in droplets, in the bottom.

The compositions converted to the gas phase can preferably be condensed (condensed vapours) before they are introduced into the next evaporator. Accordingly, condensers can be arranged between the different evaporators. Accordingly, a preferred plant for performing the present invention may comprise three stills connected to one another.

However, the present invention is not limited to a plant with three evaporators or three stills. In further embodiments, an inventive plant may have four, five or more evaporators which are connected to one another according to the principle detailed above, such that a circuit is formed in each case between two evaporators.

For further illustration, the present invention is described with reference to the FIGURE without any intention that this should impose a restriction of the invention.

BRIEF DESCRIPTION OF THE DRAWING

The FIGURE shows, in the schematic illustration, a preferred plant for performing the present invention. The hydroxyalkyl (meth)acrylate obtained from production is introduced into a first circulation evaporator (1) via mass flow (2). The circulation evaporator can be operated at a pressure in the range from 1 mbar to 10 mbar, which gives rise, according to the ester, to a temperature range from 55° C. to 120° C. The distillate is condensed and passed out of the plant via mass flow (3). The condenser needed for this purpose may form one unit with the evaporator or be configured as a separate unit. The unevaporated proportion of the ester fed in is passed via mass flow (4) into the second circulation evaporator (5), in which a majority of the ester passed in is evaporated and, after condensation, transferred into the first circulation evaporator (1) via mass flow (6). The residue formed in the second circulation evaporator (5) is passed into the thin-film evaporator (8) via mass flow (7). In thin-film evaporator (8), a portion of the mixture passed in is likewise converted to the gas phase, condensed and introduced into the second circulation evaporator (5) via mass flow (9). The residue remaining in the thin-film evaporator (8) is discharged from the plant via mass flow (10).

FIG. 1 shows, in the schematic illustration, a preferred plant for performing the present invention.

The hydroxyalkyl (meth)acrylate obtained from production is introduced into a first circulation evaporator (1) via mass flow (2). The circulation evaporator can be operated at a pressure in the range from 1 mbar to 10 mbar, which gives rise, according to the ester, to a temperature range from 55° C. to 120° C. The distillate is condensed and passed out of the plant via mass flow (3). The condenser needed for this purpose may form one unit with the evaporator or be configured as a separate unit. The unevaporated proportion of the ester fed in is passed via mass flow (4) into the second circulation evaporator (5), in which a majority of the ester passed in is evaporated and, after condensation, transferred into the first circulation evaporator (1) via mass flow (6). The residue formed in the second circulation evaporator (5) is passed into the thin-film evaporator (8) via mass flow (7). In thin-film evaporator (8), a portion of the mixture passed in is likewise converted to the gas phase, condensed and introduced into the second circulation evaporator (5) via mass flow (9). The residue remaining in the thin-film evaporator (8) is discharged from the plant via mass flow (10).

The evaporators (5) and (8) are preferably likewise operated at a pressure in the range from 1 to 10 mbar and a temperature in the range from 55 to 120° C. The plant is preferably adjusted such that the ratio of the mass flow with which the purified compound is discharged from the plant via mass flow (3) to the mass flow with which the hydroxyalkyl (meth)acrylate obtained from production is introduced into the plant via mass flow (2) is in the range from 0.85 to 0.97, preferably 0.90 to 0.95.

Particularly advantageously, high-boiling compounds are transferred with a high mass flow from the first circulation evaporator (1) through line (4) into the second circulation evaporator (5). The ratio of the mass flow with which high-boiling compounds are transferred from the first circulation evaporator (1) through line (4) into the second circulation evaporator (5) to the mass flow with which the hydroxyalkyl (meth)acrylate obtained from production is introduced via line (2) into the plant is preferably in the range from 0.75 to 2, more preferably in the range from 1.20 to 1.80.

Appropriately, the ratio of the mass flow with which the vapours condensed into the second circulation evaporator (5) are transferred via line (6) into the first circulation evaporator (1) to the mass flow with which the hydroxyalkyl (meth)acrylate obtained from production is introduced via line (2) into the plant is in the range from 0.75 to 1.90, more preferably in the range from 1.25 to 1.75, without any intention that this should impose a restriction.

The residue of high-boiling compounds obtained in the second evaporator (5) is introduced into the thin-film evaporator (8). In this case, the plant is preferably adjusted such that the ratio of the mass flow with which these high-boiling compounds are transferred via line (7) into the thin-film evaporator (8) to the mass flow with which the hydroxyalkyl (meth)acrylate obtained from production is introduced via line (2) into the plant is in the range from 0.05 to 1.25, more preferably 0.10 to 0.50.

The gas phase formed in the thin-film evaporator (8) is, after condensation, transferred into the second circulation evaporator (5). The ratio of the mass flow with which the condensed vapours are transferred into the second circulation evaporator (5) to the mass flow with which the hydroxyalkyl (meth)acrylate obtained from production is introduced via line (2) into the plant is preferably in the range from 0.01 to 1.20, more preferably 0.05 to 0.50.

The residue obtained in thin-film evaporator (8) is discharged from the plant. Appropriately, the ratio of the mass flow with which the residue obtained in thin-film evaporator (8) is discharged from the plant to the mass flow with which the hydroxyalkyl (meth)acrylate obtained from production is introduced into the plant via line (2) is 0.03 to 0.15, more preferably 0.05 to 0.10.

The plant according to the FIGURE has been described in connection with hydroxyalkyl (meth)acrylates. The mass flows, especially the ratios of the individual mass flows, apply correspondingly to other unsaturated compounds, especially other glycol esters. The same applies to plants which comprise other evaporator types or more than three evaporators. If the mixture to be purified is passed into the plant via more than one mass flow, the values stated above apply to the mass flows with which the total amount is passed into the plant.

The invention will be illustrated hereinafter with reference to examples, without any intention that this should impose a restriction.

EXAMPLE 1

In a plant shown in the FIGURE, 2-hydroxyethyl methacrylate was purified in a prolonged test which was carried out over 14 days. The first circulation evaporator (1) was operated at a pressure of approximately 2 mbar-3 mbar and a temperature of approximately 66° C.-72° C. The feed rate with which the 2-hydroxyethyl methacrylate obtained from production carried out beforehand was introduced via line (2) into the plant was on average 1.605 kg/h. The mass flow with which the vapours obtained from the first circulation evaporator (1) were passed out of the plant via line (3) was on average of 1.518 kg/h.

The residue obtained in the first circulation evaporator (1) was passed with a mass flow of on average 1.930 kg/h via line (4) into the second circulation evaporator (5). The second circulation evaporator (5) was operated at a pressure of approximately 2 mbar-3 mbar and a temperature of approximately 66° C.-74° C., and the condensed vapours were passed with a mass flow of on average 1.843 kg/h via line (6) into the first circulation evaporator (1).

The residue obtained in the second circulation evaporator (5) was passed with a mass flow of on average 0.580 kg/h via line (7) into the thin-film evaporator (8). The thin-film evaporator (8) was operated at a pressure of approximately 2 mbar-3 mbar and a temperature of approximately 68° C.-78° C., and the condensed vapours were passed with a mass flow of on average 0.493 kg/h via line (9) into the circulation evaporator (5). The resulting residue of on average 0.087 kg/h was discharged from the plant via line (10).

The 2-hydroxyethyl methacrylate introduced into the plant via line (2) had a purity of approximately 95.0%. The purified 2-hydroxyethyl methacrylate exhibited a purity of 99.1%. The yield was 49.6%.

After this prolonged test, the plants did not exhibit any traces of polymer formed.

EXAMPLE 2

In a plant described in the FIGURE, hydroxypropyl methacrylate was purified in a prolonged test which was carried out over 15 days. The first circulation evaporator (1) was operated at a pressure of approximately 2 mbar-3 mbar and a temperature of approximately 68° C.-78° C. The feed rate with which the hydroxypropyl methacrylate obtained from production carried out beforehand was introduced via line (2) into the plant was on average 1.486 kg/h. The mass flow with which the vapours obtained from the first circulation evaporator (1) were passed out of the plant via line (3) was on average of 1.403 kg/h.

The residue obtained in the first circulation evaporator (1) was passed with a mass flow of on average 1.540 kg/h via line (4) into the second circulation evaporator (5). The second circulation evaporator (5) was operated at a pressure of approximately 2 mbar-3 mbar and a temperature of approximately 70° C.-78° C., and the condensed vapours were passed with a mass flow of on average 1.475 kg/h via line (6) into the first circulation evaporator (1).

The residue obtained in the second circulation evaporator (5) was passed with a mass flow of on average 0.680 kg/h via line (7) into the thin-film evaporator (8). The thin-film evaporator (8) was operated at a pressure of approximately 2 mbar-3 mbar and a temperature of approximately 72° C.-82° C., and the condensed vapours were passed with a mass flow of on average 0.615 kg/h via line (9) into the circulation evaporator (5). The resulting residue of on average 0.065 kg/h was discharged from the plant via line (10).

The hydroxypropyl methacrylate introduced into the plant via line (2) had a purity of approximately 95.8%. The purified hydroxypropyl methacrylate exhibited a purity of 99.1% of target product. The yield was 94.4%. After this prolonged test, the plants did not exhibit any traces of polymer formed.

EXAMPLE 3

In a plant detailed in the FIGURE, 2-hydroxyethyl acrylate was purified in a prolonged test which was carried out over 11 days. The first circulation evaporator (1) was operated with a pressure of approximately 2 mbar-3 mbar and a temperature of approximately 58° C.-68° C. The feed rate with which the 2-hydroxyethyl acrylate obtained from production carried out beforehand was introduced into the plant via line (2) was on average 1.330 kg/h. The mass flow with which the vapours obtained from the first circulation evaporator (1) were passed out of the plant via line (3) was on average of 1.060 kg/h.

The residue obtained in the first circulation evaporator (1) was passed with a mass flow of on average 2.010 kg/h via line (4) into the second circulation evaporator (5). The second circulation evaporator (5) was operated at a pressure of approximately 2 mbar-3 mbar and a temperature of approximately 60° C.-68° C., and the condensed vapours were passed with a mass flow of on average 1.740 kg/h via line (6) into the first circulation evaporator (1).

The residue obtained in the second circulation evaporator (5) was passed with a mass flow of on average 0.930 kg/h via line (7) into the thin-film evaporator (8). The thin-film evaporator (8) was operated at a pressure of approximately 2 mbar-3 mbar and a temperature of approximately 62° C.-72° C., and the condensed vapours were passed with a mass flow of on average 0.660 kg/h via line (9) into the circulation evaporator (5). The resulting residue of on average 0.270 kg/h was discharged from the plant via line (10).

The 2-hydroxyethyl acrylate introduced into the plant via line (2) had a purity of approximately 85.3%. The purified 2-hydroxyethyl acrylate exhibited a purity of 99.0%. The yield was 79.7%. After this prolonged test, the plant exhibited only very small traces of polymer formed.

COMPARATIVE EXAMPLE 1

In a plant consisting of a circulation evaporator and a column, 2-hydroxyethyl methacrylate was purified in a prolonged test which was carried out over 14 days. The plant was operated with a pressure of approximately 2 mbar-3 mbar and a temperature of approximately 65° C.-73° C. The feed rate with which the 2-hydroxyethyl methacrylate obtained from production carried out beforehand was introduced into the middle of the column was on average 1.605 kg/h. The mass flow with which the resulting vapours were passed out of the column via the top was on average 1.495 kg/h. The resulting residue of on average 0.110 kg/h was discharged from the plant from the circulation evaporator.

The 2-hydroxyethyl methacrylate introduced into the plant had a purity of approximately 95.0%. The purified 2-hydroxyethyl methacrylate exhibited a purity of 98.5%. The yield was 93.1%.

After this prolonged test, the plant exhibited considerable traces of polymer formed.

COMPARATIVE EXAMPLE 2

In a plant consisting of a circulation evaporator and a column, hydroxypropyl methacrylate was purified in a prolonged test which was carried out over 15 days. The plant was operated with a pressure of approximately 2 mbar-3 mbar and a temperature of approximately 67° C.-79° C. The feed rate with which the hydroxypropyl methacrylate obtained from production carried out beforehand was introduced into the middle of the column was on average 1.486 kg/h. The mass flow with which the resulting vapours were passed out of the column via the top was on average 1.390 kg/h. The resulting residue of on average 0.096 kg/h was discharged from the plant from the circulation evaporator.

The hydroxypropyl methacrylate introduced into the plant had a purity of approximately 95.0%. The purified hydroxypropyl methacrylate exhibited a purity of 98.7%. The yield was 93.5%.

After this prolonged test, the plant exhibited considerable traces of polymer formed.

COMPARATIVE EXAMPLE 3

In a plant consisting of a circulation evaporator and a column, 2-hydroxyethyl acrylate was purified in a prolonged test which was carried out over 8 days. The plant was operated with a pressure of approximately 2 mbar-3 mbar and a temperature of approximately 56° C.-70° C. The feed rate with which the 2-hydroxyethyl acrylate obtained from production carried out beforehand was introduced into the middle of the column was on average 1.330 kg/h. The mass flow with which the vapours obtained were passed out of the column via the top was on average 0.950 kg/h. The resulting residue of on average 0.380 kg/h was discharged from the plant from the circulation evaporator.

The 2-hydroxyethyl acrylate introduced into the plant had a purity of approximately 85.3%. The purified 2-hydroxyethyl acrylate exhibited a purity of 98.5%. The yield was 71.4%.

After 8 days, the plant had to be shut down owing to considerable amounts of polymer formed.

The invention claimed is:

1. A process for purifying an unsaturated compound, wherein said purification is performed in a plant comprising at least three evaporators, wherein one circuit is formed between a first and a second evaporator, and one circuit is formed between the second and a third evaporator, wherein a portion of the unsaturated compound is circulated; vapours condensed in the first evaporator are isolated; the vapours condensed in the second evaporator are introduced into the first evaporator; and a mass flow with which the condensed vapours are isolated from a mixture to be purified in the first evaporator is less than the mass flow with which the condensed vapours from the second evaporator are introduced into the first evaporator.

2. The process according to claim 1, wherein the unsaturated compound is a glycol ester.

3. The process according to claim 2, wherein the glycol ester is a hydroxyalkyl (meth)acrylate.

4. The process according to claim 1, wherein the ratio of the mass flow with which the vapours condensed in the first evaporator are isolated from the mixture to be purified to the mass flow with which the condensed vapours from the second evaporator are introduced into the first evaporator is in the range from 0.5 to 0.8.

5. The process according to claim 1, wherein the plant comprises three evaporators.

6. The process according to claim 1, wherein the ratio of the mass flow with which the condensed vapours from the second evaporator are introduced into the first evaporator to the mass flow with which the condensed vapours of the third evaporator are introduced into the second evaporator is in the range from 0.75 to 35.

7. The process according to claim 1, wherein at least a portion of the mixture to be purified is first introduced into the first evaporator.

8. The process according to claim 1, wherein at least a portion of the mixture to be purified is first introduced into the second evaporator.

9. The process according to claim 7, wherein at least a portion of the mixture to be purified is first introduced into the first evaporator and a further portion of the mixture to be purified is first introduced into the second evaporator.

10. The process according to claim 9, wherein a quantitative ratio of the portion of the mixture to be purified introduced into the first evaporator to the portion of the mixture to be purified introduced into the second evaporator is in the range from 9:1 to 0.1:1.

11. The process according to claim 1, wherein the first evaporator is a circulation evaporator.

12. The process according to claim 1, wherein the second evaporator is a circulation evaporator.

13. The process according to claim 1, wherein at least one of the first and the second evaporator is a forced-circulation evaporator.

14. The process according to claim 1, wherein at least one of the first and the second evaporator is a natural-circulation evaporator.

15. The process according to claim 1, wherein the third evaporator is a thin-film evaporator.

16. The process according to claim 1, wherein a reactant is converted to a gas phase at a pressure in the range from 0.1 mbar to 20 mbar.

17. The process according to claim 1, wherein the unsaturated compound is converted to a gas phase at a temperature in the range from 40° C. to 120° C.

18. The process according to claim 17, wherein the gas loading factor is in the range from 0.8 to 3.0 $Pa^{0.5}$.

19. A process for purifying an unsaturated compound, wherein said purification is performed in a plant comprising at least two connected evaporators, wherein a portion of the unsaturated compound is circulated; vapours condensed in a first evaporator are isolated; the vapours condensed in a second evaporator are introduced into the first evaporator; and a mass flow with which the condensed vapours are isolated from a mixture to be purified in the first evaporator is less than the mass flow with which the condensed vapours from the second evaporator are introduced into the first evaporator,
  wherein one of the following limitations a)-d) are present:
  a) the first evaporator is a circulation evaporator;
  b) the second evaporator is a circulation evaporator;
  c) at least one of the first and the second evaporator is a forced-circulation evaporator;
  d) at least one of the first and the second evaporator is a natural-circulation evaporator.

20. The process according to claim 19, wherein the first evaporator is a circulation evaporator.

21. The process according to claim 19, wherein the second evaporator is a circulation evaporator.

22. The process according to claim 19, wherein at least one of the first and the second evaporator is a forced-circulation evaporator.

23. The process according to claim 19, wherein at least one of the first and the second evaporator is a natural-circulation evaporator.

24. The process according to claim 19, wherein the unsaturated compound is a glycol ester.

25. The process according to claim 24, wherein the glycol ester is a hydroxyalkyl (meth)acrylate.

26. The process according to claim 19, wherein the ratio of the mass flow with which the vapours condensed in the first evaporator are isolated from the mixture to be purified to the mass flow with which the condensed vapours from the second evaporator are introduced into the first evaporator is in the range from 0.5 to 0.8.

* * * * *